(12) United States Patent
Hawthorne et al.

(10) Patent No.: US 7,900,526 B2
(45) Date of Patent: Mar. 8, 2011

(54) DEFECT CLASSIFICATION UTILIZING DATA FROM A NON-VIBRATING CONTACT POTENTIAL DIFFERENCE SENSOR

(75) Inventors: Jeffrey Alan Hawthorne, Decatur, GA (US); M. Brandon Steele, Decatur, GA (US); Yeyuan Yang, Marietta, GA (US); Mark Schulze, Austin, TX (US)

(73) Assignee: QCEPT Technologies, Inc., Atlanta, GA (US)

( * ) Notice: Subject to any disclaimer, the term of this patent is extended or adjusted under 35 U.S.C. 154(b) by 609 days.

(21) Appl. No.: 11/948,518

(22) Filed: Nov. 30, 2007

(65) Prior Publication Data

US 2009/0139312 A1    Jun. 4, 2009

(51) Int. Cl.
  *G01N 33/00*    (2006.01)
(52) U.S. Cl. ......................................................... 73/866
(58) Field of Classification Search .......................... None
  See application file for complete search history.

(56) References Cited

U.S. PATENT DOCUMENTS

| | | | |
|---|---|---|---|
| 4,166,974 A | 9/1979 | Vermeers | |
| 4,295,092 A | 10/1981 | Okamura | |
| 4,481,616 A | 11/1984 | Matey | |
| 4,767,211 A | 8/1988 | Munakata et al. | |
| 4,973,910 A | 11/1990 | Wilson | |
| 5,087,533 A | 2/1992 | Brown | |
| 5,136,247 A | 8/1992 | Hansen | |
| 5,214,389 A | 5/1993 | Cao et al. | |
| 5,217,907 A | 6/1993 | Bulucea et al. | |
| 5,218,362 A | 6/1993 | Mayes et al. | |
| 5,270,664 A | 12/1993 | McMurtry et al. | |
| 5,272,443 A | 12/1993 | Winchip et al. | |
| 5,278,407 A | 1/1994 | Ikebe et al. | |
| 5,293,131 A | 3/1994 | Semones et al. | |
| 5,315,259 A | 5/1994 | Jostlein | |
| 5,369,370 A | 11/1994 | Stratmann et al. | |
| 5,381,101 A | 1/1995 | Bloom et al. | |
| 5,460,684 A | 10/1995 | Saeki et al. | |
| 5,517,123 A | 5/1996 | Zhao et al. | |
| 5,546,477 A | 8/1996 | Knowles et al. | |
| 5,583,443 A | 12/1996 | McMurtry et al. | |
| 5,723,980 A | 3/1998 | Haase et al. | |
| 5,723,981 A | 3/1998 | Hellemans et al. | |
| 5,773,989 A | 6/1998 | Edelman et al. | |

(Continued)

FOREIGN PATENT DOCUMENTS

DE    297 509 A5    1/1992

(Continued)

OTHER PUBLICATIONS

B Scruton and B.H. Blott, A High Resolution Probe for Scanning Electrostatic Potential Profiles Across Surfaces; Journal of Physics E: Scientific Instruments (May 1973), pp. 472-474; vol. 6, No. 5, Printed in Great Britain.

(Continued)

*Primary Examiner* — Robert R Raevis
(74) *Attorney, Agent, or Firm* — Foley & Lardner LLP (57) ABSTRACT

A method and system for identifying and classifying non-uniformities on the surface of a semiconductor or in a semiconductor. The method and system involves scanning the wafer surface with a non-vibrating contact potential difference sensor to detect the locations of non-uniformities, extracting features characteristic of the non-uniformities, and applying a set of rules to these features to classify the type of each non-uniformity.

21 Claims, 9 Drawing Sheets

U.S. PATENT DOCUMENTS

| | | | |
|---|---|---|---|
| 5,789,360 A | 8/1998 | Song et al. | |
| 5,974,869 A | 11/1999 | Danyluk et al. | |
| 5,977,788 A | 11/1999 | Lagowski | |
| 6,011,404 A | 1/2000 | Ma et al. | |
| 6,037,797 A | 3/2000 | Lagowski et al. | |
| 6,091,248 A | 7/2000 | Hellemans et al. | |
| 6,094,971 A | 8/2000 | Edwards et al. | |
| 6,097,196 A | 8/2000 | Verkuil et al. | |
| 6,104,481 A * | 8/2000 | Sekine et al. | 356/237.5 |
| 6,114,865 A | 9/2000 | Lagowski et al. | |
| 6,127,289 A | 10/2000 | Debusk | |
| 6,139,759 A | 10/2000 | Doezema et al. | |
| 6,198,300 B1 | 3/2001 | Doezema et al. | |
| 6,201,401 B1 | 3/2001 | Hellemans et al. | |
| 6,232,134 B1 | 5/2001 | Farber et al. | |
| 6,255,128 B1 | 7/2001 | Chacon et al. | |
| 6,265,890 B1 | 7/2001 | Chacon et al. | |
| 6,517,669 B2 | 2/2003 | Chapman | |
| 6,520,839 B1 | 2/2003 | Gonzalez-Martin et al. | |
| 6,538,462 B1 | 3/2003 | Lagowski et al. | |
| 6,546,814 B1 | 4/2003 | Choe et al. | |
| 6,551,972 B1 | 4/2003 | Lei et al. | |
| 6,597,193 B2 | 7/2003 | Lagowski et al. | |
| 6,664,546 B1 | 12/2003 | McCord et al. | |
| 6,664,800 B2 | 12/2003 | Chacon et al. | |
| 6,679,117 B2 | 1/2004 | Danyluk et al. | |
| 6,680,621 B2 | 1/2004 | Savtchouk et al. | |
| 6,711,952 B2 | 3/2004 | Leamy et al. | |
| 6,717,413 B1 | 4/2004 | Danyluk et al. | |
| 6,771,091 B2 | 8/2004 | Lagowski et al. | |
| 6,791,310 B2 | 9/2004 | Smith | |
| 6,803,241 B2 | 10/2004 | Eom et al. | |
| 6,849,505 B2 | 2/2005 | Lee et al. | |
| 6,858,089 B2 | 2/2005 | Castrucci | |
| 6,929,531 B2 | 8/2005 | Gotkis et al. | |
| 7,019,654 B2 | 3/2006 | Danyluk et al. | |
| 7,084,661 B2 | 8/2006 | Thompson et al. | |
| 7,107,158 B2 | 9/2006 | Steele et al. | |
| RE39,803 E | 9/2007 | Danyluk et al. | |
| 7,385,686 B2 * | 6/2008 | Shiba et al. | 356/237.1 |
| 7,420,669 B2 * | 9/2008 | Sopori et al. | 356/237.4 |
| 2003/0139838 A1 | 7/2003 | Marella | |
| 2003/0164942 A1 | 9/2003 | Take | |
| 2003/0175945 A1 | 9/2003 | Thompson et al. | |
| 2004/0029131 A1 | 2/2004 | Thompson et al. | |
| 2004/0057497 A1 | 3/2004 | Lagowski et al. | |
| 2004/0058620 A1 | 3/2004 | Gotkis et al. | |
| 2004/0070355 A1 | 4/2004 | Ogura | |
| 2004/0079142 A1 * | 4/2004 | Proksch | 73/105 |
| 2004/0105093 A1 | 6/2004 | Hamamatsu et al. | |
| 2004/0134515 A1 | 7/2004 | Castrucci | |
| 2004/0152250 A1 | 8/2004 | Steele et al. | |
| 2004/0241890 A1 | 12/2004 | Steele et al. | |
| 2005/0016279 A1 | 1/2005 | Hawthorne et al. | |
| 2005/0162178 A1 | 7/2005 | Steele et al. | |
| 2007/0010954 A1 | 1/2007 | Steele et al. | |

FOREIGN PATENT DOCUMENTS

| | | |
|---|---|---|
| EP | 1 039 277 | 9/2000 |
| EP | 1 304 463 B1 | 4/2003 |
| WO | WO 01/90730 A2 | 11/2001 |
| WO | WO 02/079754 A2 | 10/2002 |
| WO | WO 03/033993 A1 | 4/2003 |
| WO | WO 2004/070355 A2 | 8/2004 |

OTHER PUBLICATIONS

Yano D et al: "Nonvibrating contact potential difference probe measurement of a nanometer-scale lubricant on a hard disk", Journal of Tribology, American Society of Mechanical Engineers, New York, NY, US; vol. 121, No. 4, Oct. 1999, pp. 980-983, XP008031092, ISSN: 0742-4787 (pp. 980-981, fig. 4, first ref. on p. 983).

Castaldini A et al: "Surface analyses of polycrystalline and Cz-Si wafers", Solar Energy Materials and Solar Cells, Elsevier Science Publishers, Amsterdam, NL; vol. 72, No. 1-4, Apr. 2002, pp. 425-432, XP004339790, ISSN: 0927-0248 (whole document).

Korach C S et al: "Measurement of perfluoropolyether lubricant thickness on a magnetic disk surface", Applied Physics Letters, American Institute of Physics, New York, NY, US; vol. 79, No. 5, Jul. 30, 2001, pp. 698-700, XP012029958, ISSN: 0003-6951 (p. 699, left column; fig. 2).

Yang Y et al: "Kelvin probe study on the perfluoropolyether film on metals", Tribology Letters, 2001, Kluwer Academic/Plenum Publishers, USA, vol. 10, No. 4, pp. 211-216, XP009035197, ISSN: 1023-8883 (p. 211-p. 212).

Castaldini A et al: "Scanning Kelvin probe and surface photovoltage analysis of multicrystalline silicon", Materials Science and Engineering B., Elsevier Sequoia, Lausanne, Ch; vol. 91-92, Apr. 30, 2002, pp. 234-238, XP004355534, ISSN: 0921-5107 (chapters 2.2 Scanning Kelvin probe: and "4.2 Scanning Kelvin probe analyses").

\* cited by examiner

DEFECT CLASSIFICATION UTILIZING DATA FROM A NON-VIBRATING CONTACT POTENTIAL DIFFERENCE SENSOR

FIELD OF THE INVENTION

The present invention is directed to methods and systems for the inspection of surfaces and materials, including semiconductor surfaces and semiconductor materials. More particularly, the present invention is directed to methods for the classification of surface or subsurface non-uniformities and/or charges detected using at least one of a vibrating and a non-vibrating contact potential difference sensor.

BACKGROUND OF THE INVENTION

The function, reliability and performance of semiconductor devices depend on the use of semiconductor materials and surfaces which are clean and uniform. Billions of dollars and countless man-hours have been spent developing, characterizing, and optimizing systems and processes for fabricating and processing semiconductor materials. A primary goal of this activity has been the fabrication of materials and surfaces that are extremely clean and that have properties that are uniform, or vary uniformly, across the entire wafer. In order to characterize and optimize these processes it is necessary to be able to inspect and measure surface or bulk cleanliness and uniformity. For real-time process control, it is necessary to be able to make many measurements across a surface at high speed, and to do so in a manner that does not damage or contaminate the semiconductor surface. It is also highly desirable to be able to discriminate and classify different types of non-uniformities or contaminants. Classification is extremely important. Information on the nature of a non-uniformity can be used to determine if the non-uniformity might impact device performance or manufacturing yield. Classification information can also be used to identify the source of the non-uniformity.

One method of inspecting and measuring surfaces utilizes a non-vibrating contact potential difference sensor. The non-vibrating contact potential difference sensor consists of a conductive probe that is positioned close to a surface, and is electrically connected to the surface. The probe and the surface form a capacitor. A potential difference is formed between the probe tip and the surface due to the difference in work functions or surface potentials of the two materials. The probe tip is translated parallel to the surface, or the surface is translated beneath the probe. Changes in the work function or surface potential at different points on the surface result in changes in potential between the surface and the probe tip. Also, changes in the distance between the probe tip and the wafer surface results in changes in the capacitance. Changes in either the potential or capacitance between the probe tip and the wafer surface causes a current to flow into the probe tip. This current is amplified, converted to a voltage, and sampled to form a continuous stream of data which represents changes across the surface. The non-vibrating contact potential difference sensor can provide a continuous stream of data at rates greater than 100,000 samples per second. High data acquisition rates permit high-resolution images of whole semiconductor wafers to be acquired in only a few minutes.

The non-vibrating contact potential difference sensor produces a signal that is a combination of two characteristics of the measured surface-changes in surface potential and changes in surface height. The charge on the probe tip is determined as follows:

$$Q = CV \quad (1)$$

Where Q is the charge on the probe tip, C is the capacitance between the probe tip and the measured surface, and V is the potential difference between the probe tip and the surface.

The current, i, into the probe tip is the derivative of the charge on the probe tip and is given by the following formula:

$$i = \frac{dQ}{dt} = C\frac{dV}{dt} + V\frac{dC}{dt} \quad (2)$$

The current, i, is the sum of two terms: the dV/dt term and the dC/dt term. The dV/dt term represents changes in the voltage between the probe tip and the wafer surface, and the dC/dt term represents changes in the capacitance between the probe tip and the wafer surface. The potential of the probe tip is fixed during the scanning operation, so changes in the dV/dt term arise from changes in the potential of the measured surface. Changes in capacitance result from changes in the distance between the probe tip and the wafer surface, which most often result from changes in the height of the wafer surface. This formula illustrates how the current into the sensor is a combination of changes in the potential and height of the measured surface.

Changes in surface potential can result from a variety of changes in surface and subsurface conditions. These include; but are not limited to; contamination by metals, contamination by non-metals or organics, changes in surface chemistry, changes in the number or type of molecules from the environment that adsorb on the surface, changes in the chemical termination of the surface, charging on the surface, charging in a dielectric deposited on the surface, changes in the atomic roughness of the surface, changes in surface film stress, changes in subsurface doping density or implant dose, changes in subsurface doping or implant depth, changes in potential at subsurface interfaces, changes in subsurface electrical conductivity, changes in crystalline structure or damage, changes in surface illumination, or some combination of these factors.

The non-vibrating contact potential difference sensor system can detect a wide range of surface and subsurface non-uniformities. However, it would be desirable to enhance the capabilities of the non-vibrating contact potential difference sensor inspection system to enable the discrimination and classification of different types of non-uniformities. For example, it would be desirable to discriminate between surface potential non-uniformities resulting from metallic contamination and surface potential non-uniformities resulting from organic contamination. As a second example, it would be desirable to discriminate between surface chemical contamination and variations in the height of the wafer surface.

SUMMARY OF THE INVENTION

The system and methods described in this invention provide an enhanced application of at least one of a vibrating and a non-vibrating contact potential difference inspection system that allows the discrimination and classification of different types of surface and subsurface non-uniformities. Hereinafter, material susceptible to inspection by the system herein described will be denoted generally as a "wafer". The invention includes at least one of a vibrating and a non-vibrating contact potential difference sensor scanning system that generates data representative of surface potential and height variations across the wafer surface. This apparatus consists of at least one of a vibrating and a non-vibrating contact potential difference sensor, a system for mechanically fixturing the wafer, a system for positioning the sensor a fixed distance above the wafer surface and generating relative motion between the probe tip and wafer surface such that the sensor probe tip moves parallel to the wafer surface, and a system for acquiring and processing the output signal from the sensor to identify and classify wafer non-uniformities.

In one embodiment, the system includes the ability to apply a bias voltage to either the sensor probe tip or the wafer surface to modify the electrical potential between the probe tip and wafer. In this case the dC/dt term in equation 2 includes a bias voltage as shown in the following formula:

$$i = C\frac{dV}{dt} + (V_{CPD} + V_{bias})\frac{dC}{dt} \quad (3)$$

In equation 3, $V_{CPD}$ is the voltage between the probe tip and wafer surface that results solely from electrically connecting the probe tip and the wafer surface. This voltage is called the Contact Potential Difference, or CPD. $V_{bias}$ is an additional voltage that is applied to the probe tip or wafer by the inspection system to facilitate detection and classification of wafer non-uniformities. If $V_{bias}$ is constant during the scanning operation, then it does not affect the dV/dt term because $dV_{bias}/dt=0$.

In an alternative embodiment the system includes a mechanism for positioning the sensor above a point on the wafer and vibrating the sensor perpendicular to the wafer surface while the bias voltage is adjusted. Vibrating the probe tip perpendicular to the wafer surface causes changes in the capacitance between the probe tip and the wafer surface, which results in a signal due to the VdC/dt term in equations 2 and 3. This signal is proportional to the contact potential difference (V) between the probe tip and the wafer surface. The variable bias is adjusted to determine the bias voltage that matches the potential of the probe tip to the potential of the wafer surface. When the bias voltage is equal and opposite to the contact potential difference between the probe and the wafer then the signal from the sensor goes to zero. By adjusting the bias voltage, the bias that results in zero signal is determined, and the contact potential difference is calculated as the negative of this bias voltage. This method of operation is known as a vibrating Kelvin probe or Kelvin-Zisman probe.

In another alternative embodiment the system includes the ability to control the illumination of the wafer surface near the probe tip. This capability allows the wavelength, light intensity or angle of illumination to be configured prior to, as well as during, scanning the surface using the non-vibrating contact potential difference sensor. In yet another alternative embodiment the system includes the ability to deposit charge on the wafer surface prior to the surface being scanned by the non-vibrating contact potential difference sensor. A non-uniformity can also be evaluated by measuring a charge which is deposited or otherwise present on the wafer, or on or in a dielectric layer on the wafer. The non-uniformity can include a charge itself on or in the wafer, or on or in the dielectric layer itself. In addition a change of signal arising from the deposited charge can enable identification of the type and amount of the non-uniformity.

The invention includes a system and methods for processing the resulting non-vibrating contact potential difference data to discriminate between a wide range of different types of surface non-uniformities. In an alternative embodiment, the system includes the ability to obtain multiple scans of the same wafer, or multiple scans of the same part of the same wafer. Each of the multiple scans can be acquired with different bias voltages, illumination wavelengths, illumination intensities, illumination angles; and/or with different amounts of charge applied to, or otherwise present on the surface or embedded into selected layers of a wafer and deposited layers, such as dielectrics. Data from these multiple scans can be processed separately or combined to discriminate between different types and relative amounts of non-uniformities, such as chemical, mechanical and charges.

The non-vibrating contact potential difference data is processed to identify regions of wafer non-uniformity. In one embodiment, this is accomplished by thresholding the differential non-vibrating contact potential difference image. Thresholding involves identifying those data points with specific values, where the specific values are defined as those signal values that are greater than a particular value, less than a particular value, or within some range of values. The particular values used to define areas of wafer non-uniformity are referred to as thresholds. In an alternative embodiment, non-uniformities are identified by integrating the differential data to form an image that represents relative surface potential values. The resulting integrated image can be thresholded to identify regions with specific relative surface potential values or ranges of values. Once regions of non-uniformity are identified, additional processing is performed to classify each region.

In one embodiment, the integrated image data for regions of non-uniformity are compared to the integrated image data for other parts of the wafer to determine if the non-uniformity results in a positive or negative change in surface potential or capacitance. If a non-uniformity represents a change in surface potential, then the direction (positive or negative) of the signal indicates whether the surface potential is increasing or decreasing. If a non-uniformity represents a change in surface height, then the direction of the signal indicates whether the wafer height is increasing or decreasing. This information is then used to classify non-uniformities based on the direction of surface potential or surface height change. For example, surface contamination may result in an increase or decrease in wafer surface potential. Many, but not all, types of metal contamination on silicon surfaces result in an increase in surface potential, while many types of organic contamination on silicon surfaces results in a decrease in surface potential. In inspection applications where likely metal contaminants increase surface potential and likely organic contaminants decrease surface potential, the direction of surface potential change can be used to distinguish between metallic surface contamination and organic surface contamination. Independent data can be used to assist in determining the likelihood of contaminants or non-uniformities being of a particular class, such as metal, non-metal, semiconductor dopants, insulators and ionic impurities. Such independent data can arise from use of other conventional devices, such as SEM, X-ray fluorescence, ion probe, and straightforward evaluation of the likely contaminants from a particular manufacturing process.

The signal component that results from changes in the distance between the probe tip and the wafer surface varies linearly with the voltage between the probe tip and the wafer surface, while the signal component resulting from changes in surface potential is unaffected by a constant bias voltage. As a result, the same wafer can be scanned twice with two different bias voltages, and the resulting images subtracted from each other, to form an image that has minimal signal from surface potential changes and an increased signal from height changes. This is illustrated by the following equations:

$$i_1 = C\frac{d(V_{CPD})}{dt} + C\frac{d(V_{bias1})}{dt} + (V_{CPD} + V_{bias1})\frac{dC}{dt}$$

$$i_2 = C\frac{d(V_{CPD})}{dt} + C\frac{d(V_{bias2})}{dt} + (V_{CPD} + V_{bias2})\frac{dC}{dt}$$

$$i_{1-2} = (V_{bias1} - V_{bias2})\frac{dC}{dt}$$

$$\frac{d(V_{bias1})}{dt} = 0$$

$$\frac{d(V_{bias2})}{dt} = 0$$

In this case, $i_1$ is the current into the probe tip when a bias voltage of $V_{bias1}$ is applied, and $i_2$ is the current into the probe tip when a bias voltage of $V_{bias2}$ is applied. Because the derivative of the bias voltages is 0, subtracting the two currents results in a new signal that is unaffected by changes in contact potential difference and is formed solely from changes in capacitance between the probe tip and wafer surface. The resulting signal or image can be used to detect and classify non-uniformities as variations in wafer height as opposed to changes in wafer surface potential. Likewise, non-uniformities that appear in an image acquired with no bias voltage, but do not appear in an image that is formed by subtracting two images acquired with different bias voltages, can be classified as a surface potential change as opposed to a surface height change.

The average contact potential difference between the probe tip and the wafer surface can be determined by making vibrating Kelvin probe measurements at one or more points on the wafer surface. A bias voltage which is equal in magnitude, but opposite in polarity, can then be applied to the probe tip to minimize the average difference in potential between the probe tip and wafer surface. The wafer can then be scanned using this bias voltage, and the signal component due to changes in the distance between the probe tip and the wafer surface will be minimized. Subsequent wafers with similar surfaces can also be scanned using the same bias voltage without the need to make additional vibrating Kelvin probe measurements. The use of a bias voltage which minimizes the average potential between the probe tip and the wafer surface permits the formation of a signal and image which can be used to identify non-uniformities in surface potential while minimizing the signal due to changes in the height.

One advantage of the non-vibrating contact potential difference sensor is that it can acquire data relatively quickly, so that whole-wafer images can be acquired in only a few minutes. The availability of high-resolution images permits the use of image processing algorithms to classify non-uniformities based on features associated with their shape or signal levels. For example, the differential or integrated image can be thresholded, and the resulting defect map can be segmented to identify connected regions of non-uniformity. Each region can then be associated with a list of features; such as area, perimeter, height, width, signal range, average signal value, minimum and maximum signal values, and many others. These features can be calculated from the differential or integrated images of the non-uniformities, or from images acquired with different bias voltages, illumination configurations, surface charge conditions, or combinations of these images. This list of features can then be used to classify the defect based on a mathematical algorithm or set of rules. For example, in the simplest case non-uniformities can be classified based on size or standard deviation of the non-vibrating contact potential difference sensor signal.

The ability to control the intensity, wavelength, and angle of illumination; and the amount of charge on the wafer surface or embedded in dielectric or other layers present on the wafer provides additional methods of classifying defects or location and amounts of charge. The surface potential change resulting from some types of defects is sensitive to surface illumination or charging. Illumination can be used to vary the surface potential by reducing the effect of electric fields in the semiconductor, while charge deposited or otherwise present on the surface, or in or on a dielectric layer, can be used to induce electric fields and vary the distribution of charge within the semiconductor. The ability to control the illumination and surface charge allows two or more scans to be acquired with different illumination and/or charge conditions. These scans can then be combined mathematically, for example by subtracting one scan image from another, to determine the change in signal due to changes in illumination or charge. Surface non-uniformities can then be classified based on the magnitude and polarity of the change in signal that results from changing illumination or changing surface charge conditions.

The vibrating Kelvin probe measurement capability provides yet another method of classifying defects. Once a defect has been detected and located within a non-vibrating contact potential difference image, one or more vibrating Kelvin probe measurements can be made to determine the contact potential difference at the location of the defect. The resulting contact potential difference data can be correlated to specific types or concentrations of defects, and this information can be used to identify or quantify the detected defect. Also, vibrating Kelvin probe measurements can be made with different surface charge or illumination conditions to determine the absolute change in surface potential with changing illumination variables or charging of the wafer or other attached layer. This information can also be used to classify the type of defect.

Another method of defect classification involves integrating the signal obtained from the non-vibrating contact potential difference sensor, and then making two or more vibrating Kelvin probe measurements at different points on the wafer. The integrated signal represents relative surface potential values, but does not represent absolute contact potential difference values. The vibrating Kelvin probe measurements can be used to scale the integrated signal values so that they represent absolute contact potential difference values. This is accomplished by calculating a linear or curve fit between the vibrating Kelvin probe measurements and the signal values at the same locations within the integrated image. This transformation is then applied to all integrated signal values. The resulting integrated image values can then be used to classify surface non-uniformities based on their absolute contact potential difference values.

BRIEF DESCRIPTION OF THE DRAWINGS

FIGS. 4A-4C show three different images where FIG. 4A was formed by integrating the signal in the image in FIG. 3A.

FIGS. 5A-5C show three images, and the image of FIG. 5A was created by scanning a wafer with a non-vibrating contact potential difference sensor with no surface illumination.

DETAILED DESCRIPTION OF THE PREFERRED EMBODIMENTS

The present invention provides an enhanced inspection system that uses a non-vibrating contact potential difference sensor system to detect surface and sub-surface non-uniformities, including deposited (or otherwise present) charge, and a system for processing data from the non-vibrating contact potential difference sensor to classify different types and relative amounts of non-uniformities. This invention is not limited to the measurement of semiconductors with bare, clean surfaces. The chemical state of the surface may vary, or surface contamination may be present. Also, the wafer surface may be covered with a coating or film. For example, a silicon wafer surface is often coated with a silicon oxide or other dielectric or metal film. This invention can be used to inspect a wafer covered with a film to detect defects in the underlying semiconductor or at the semiconductor-film interface. In addition, this invention can be used to detect or classify defects in, or on, a film.

Figure 1:
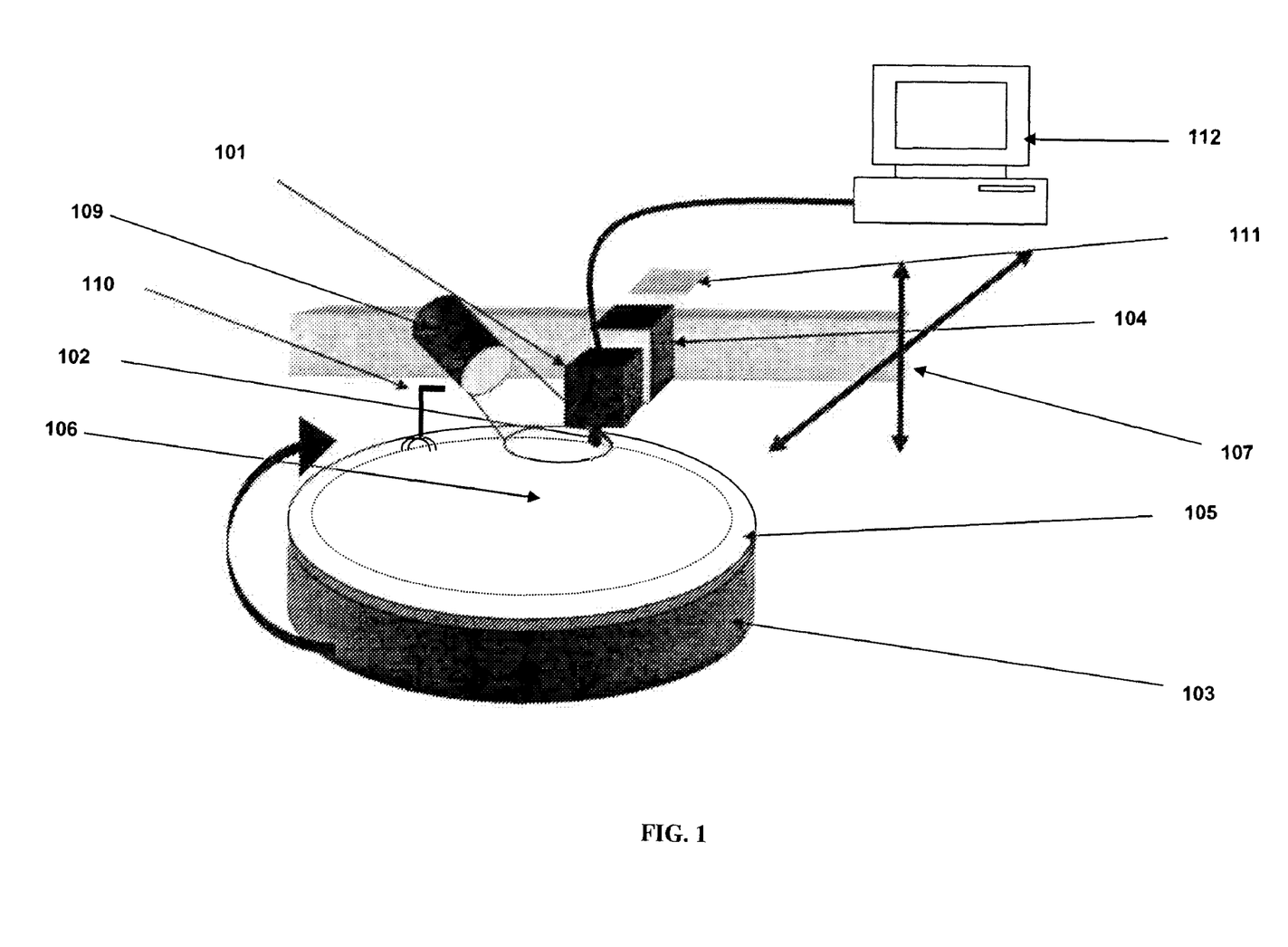
FIG. 1 is a diagram of a wafer inspection system with a non-vibrating contact potential difference sensor, a source of deposited charge, a source of controlled illumination and a system for vibrating the probe perpendicular to the wafer surface to make vibrating Kelvin probe measurements, the system including a component for processing data from the sensor, automatically detecting surface or sub-surface non-uniformities, and classifying the non-uniformities.

Referring to FIG. 1, the apparatus consists of a non-vibrating contact potential difference sensor 101, a system 103 for mechanically fixturing the wafer 105, a system 107 for positioning the sensor 101 a fixed distance above the wafer surface 106 and generating relative motion between the probe tip 102 and wafer surface 106 such that the sensor probe tip 102 moves parallel to the wafer surface 106, a source of illumination 109 with variable intensity, angle, or spectrum of light that can irradiate the semiconductor wafer surface 106 under or near the sensor probe tip 102, a source of charge 110 that can deposit a known amount of charge on the wafer surface 106 prior to scanning by the sensor probe tip 102, a system 104 for vibrating the probe tip perpendicular to the wafer surface, and a system 112 for acquiring and processing the output signal from the sensor 101 to identify and classify wafer 105 non-uniformities.

In one embodiment, a semiconductor wafer 105 is placed on a conductive wafer fixture 103. This may be done manually or using an automated process such as, but not limited to, a wafer handling robot. The wafer 105 is held in place such as by using vacuum. Alternative methods of holding the wafer 105 include, but are not limited to, electrostatic forces and edge gripping. In one embodiment, the fixture 103 is mounted to a spindle which can rotate the wafer 105 about its center. The non-vibrating contact potential difference sensor 101 is attached to a positioning system 107 that can adjust the height of the sensor 101 above the wafer surface 106 and can move the sensor 101 radially from at least the center of the wafer 105 to one edge of the wafer 105. The non-vibrating contact potential difference sensor 101 is electrically connected to the wafer surface 106 via the conductive wafer fixture 103. This connection can be resistive or capacitive. In one embodiment, a height sensor 111 that has been calibrated to the height of the non-vibrating contact potential difference sensor probe tip 102 is also mounted on the same positioning system 107 as the non-vibrating contact potential difference sensor 101.

Alternately, a light source 109 with variable intensity, wavelength or angle may be mounted on the positioning system such that the illuminated area includes at least the area next to the non-vibrating contact potential difference sensor probe tip 102. Alternately, a light source can be mounted separate from the positioning system so that it illuminates at least the entire area scanned by the non-vibrating contact potential difference sensor. Alternately, a source of controlled charge may be mounted on the positioning system so that a known amount of charge can be deposited on the wafer surface, or on or in a dielectric layer present on the wafer, prior to, or even during, scanning by the non-vibrating contact potential difference sensor.

In an alternate embodiment, a system 104 for vibrating the sensor 101 perpendicular to the wafer surface 106 is attached to the contact potential difference sensor. This system is used to make vibrating Kelvin probe measurements of the contact potential difference between the probe tip 102 and the wafer surface 106.

After the wafer 105 is secured to the fixture, the height sensor 111 is positioned above one or more points on the wafer surface 106 and the height of the wafer surface 106 is measured. These wafer height measurements are used to calculate the position of the non-vibrating contact potential difference sensor 101 that will produce the desired distance between the probe tip 102 and the wafer surface 106. This information is used to position the probe tip 102 at a fixed height above the wafer surface 106, and the probe tip 102 is moved to a point above the outside edge of the wafer 105. Illumination of the wafer surface may be enabled and the appropriate intensity and wavelength selected for the inspection application. Also, the appropriate amount of charge may be selected for the inspection application.

Figure 2A:
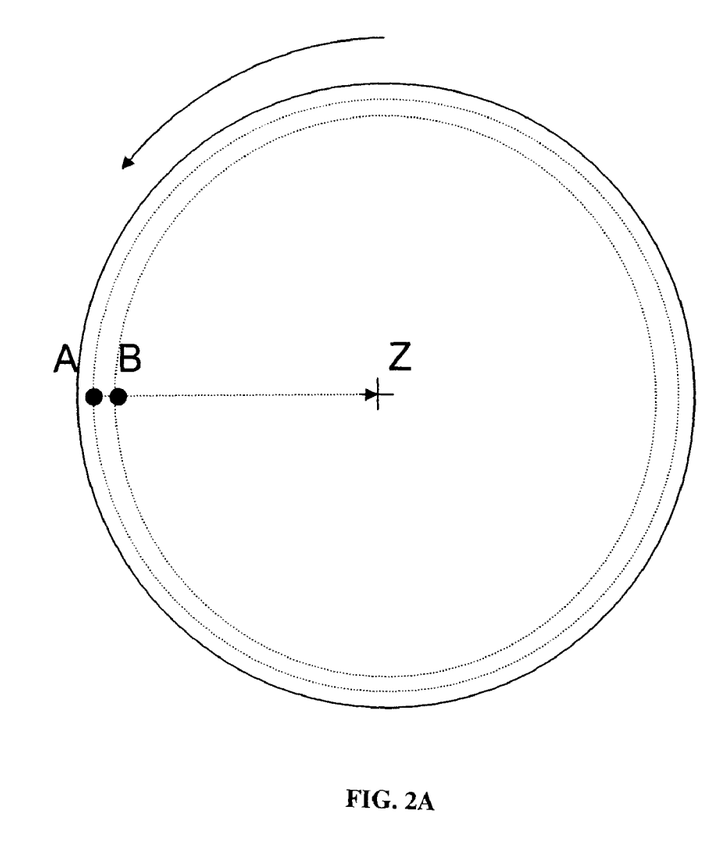
FIG. 2A shows a diagram on the left with a radial scanning system and in FIG. 2B an image on the right created by the scanning operation.

As shown for example in FIG. 2A, the probe 101 is held stationary and the wafer 105 is rotated on the spindle such that the probe tip 102 moves relative to the wafer 105 along a circular path that is centered at the wafer 105 center. Data is acquired during a single rotation of the wafer 105. The sensor 101 is then moved a programmable distance along the radius of the wafer 105 towards the wafer center. Another rotation of data is acquired at this new radius. The probe tip 102 continues to step and scan concentric circular regions of the wafer 105 until the probe reaches the wafer 105 center. The resulting data is then assembled into an image of the wafer 105. Alternately, each concentric circular region of the wafer 105 could be scanned multiple times and the resulting data averaged to reduce the effect of random noise. This image is processed to identify and classify non-uniformities (see FIG. 2B). This processing can take many forms. It may be as simple as the thresholding of signal values to detect regions of the wafer surface 106 where the surface potential is changing (compare FIGS. 3A and 3B). The differential sensor data can also be integrated to generate an image which represents relative surface potential values. This integrated image can also be processed or thresholded to identify regions with specific relative potential values. Alternately the integrated image can be calibrated using multiple vibrating Kelvin probe measurements to produce an image with values that represent the absolute contact potential difference value at each point on the wafer. This image can then be thresholded to identify regions with specific contact potential difference values.

Figure 2B:
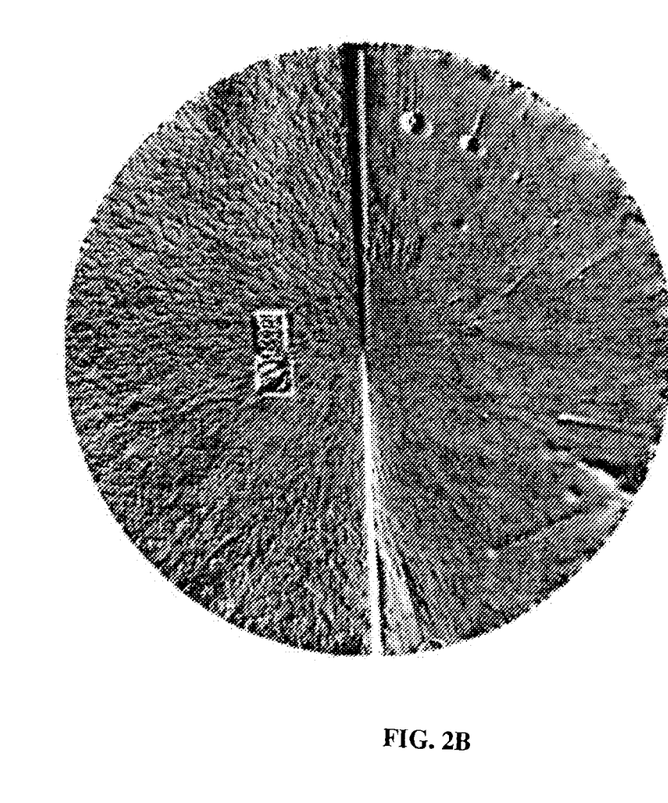

FIG. 2A show a diagram of the radial scanning of one embodiment of the present invention. The non-vibrating contact potential difference sensor probe tip 102 is positioned at point "A" near the edge of the wafer 105. The wafer 105 is rotated on the wafer fixture 103 and a circular track of data is scanned. The probe tip 102 is moved a programmable distance towards the wafer 105 center to point "B" and a second circular track of data is scanned. This process is repeated until the probe tip 102 reaches the center of the wafer 105. The resulting data is combined into an image of the wafer surface 106. A sample image is shown in FIG. 2B, and the light and dark regions representing various non-uniformities.

Figure 3A:
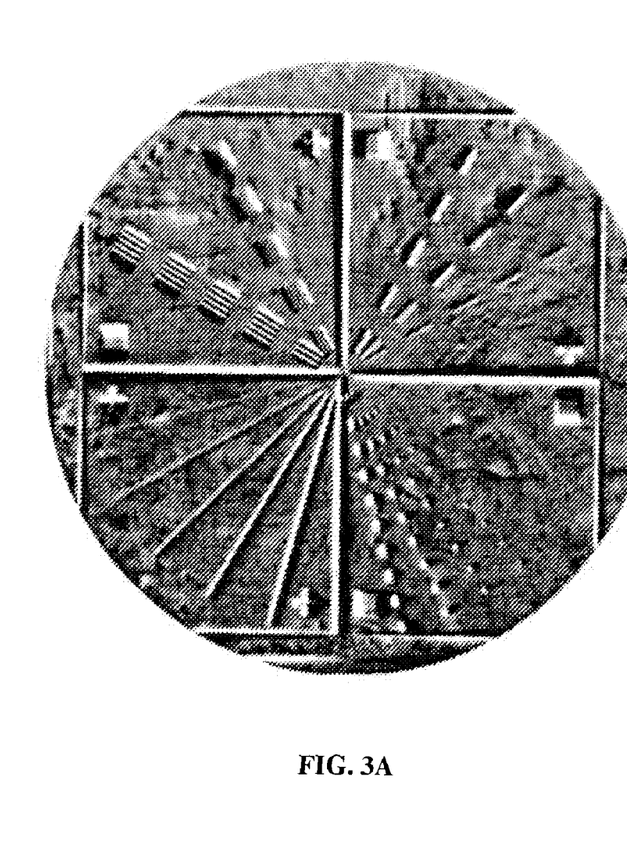
FIG. 3A shows an image created by scanning a wafer with a non-vibrating contact potential difference sensor.
Figure 3B:
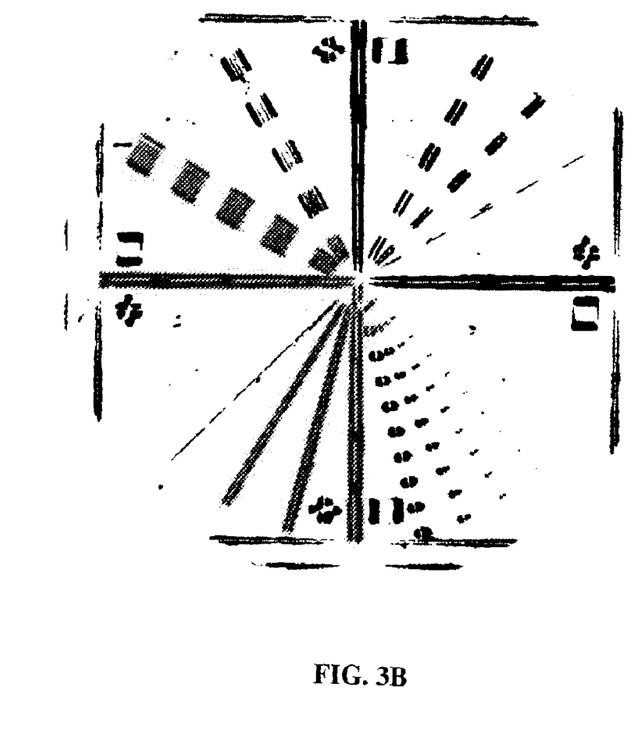
FIG. 3B is an image after thresholding where the dark regions in the thresholded image represent non-uniformities.
Figure 4A:
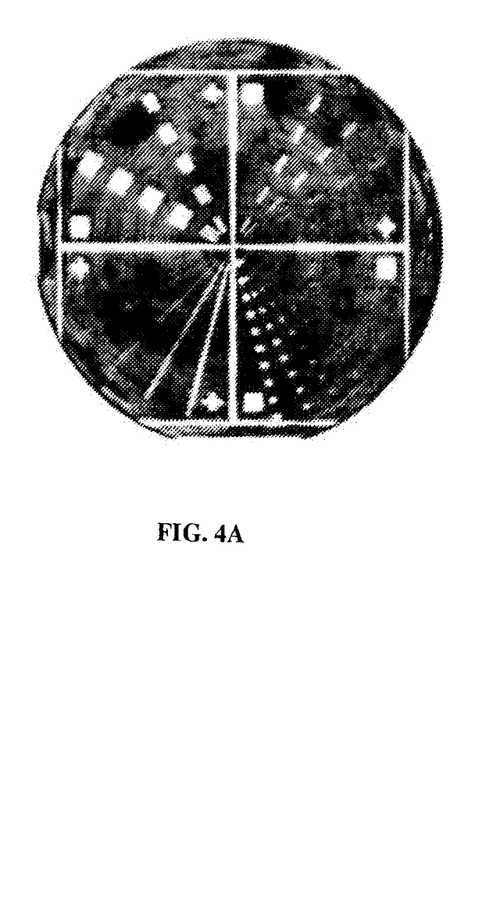
Figure 4B:
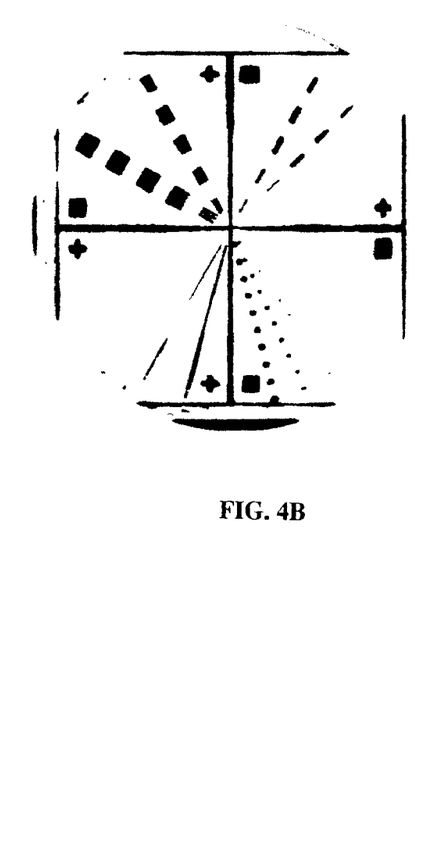
FIG. 4B shows the image after applying a threshold to identify areas of increased surface potential.
Figure 4C:
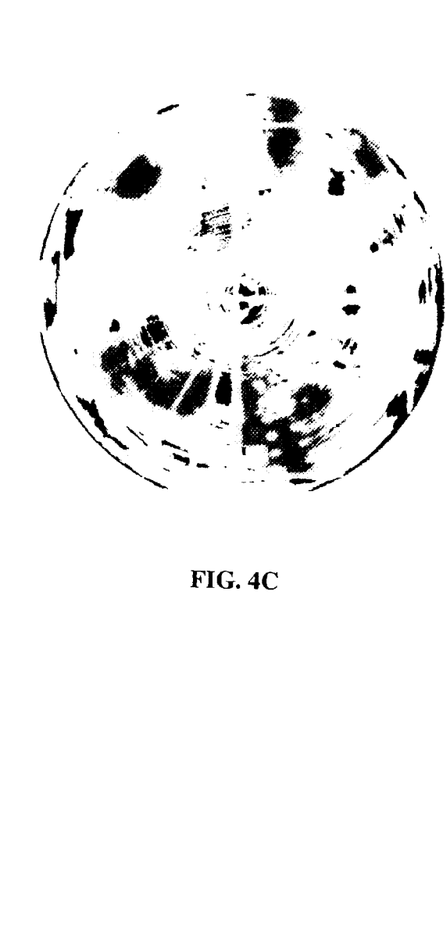
FIG. 4C shows the image after thresholding to identify regions of decreased surface potential.

One aspect of this invention is the identification or classification of non-uniformities based on the polarity of the surface potential or capacitance change. The differential non-vibrating contact potential difference sensor signal can be integrated to form a signal that represents relative surface potential or capacitance values. As shown in FIGS. 3A and 3B, this integrated signal can be thresholded to identify regions with signal values that lie within a specific range, or are above or below specified values. As shown in FIGS. 4A-4C, a non-uniformity can be classified as having a positive or negative sign based on whether the integrated signal is higher or lower than the integrated signal values for the surrounding wafer surface, or it can be classified as positive or negative based on whether the integrated signal value is higher or lower than the average integrated signal value for some portion of the wafer surface. The integrated image shows regions of relative surface potential. Some regions are bright indicating areas of FIG. 4A with increased surface potential or work function and some regions are dark indicating areas of decreased surface potential or work function. In this case the bright regions are metal patterns on the wafer and the dark regions are non-metal or organic contaminants on the wafer. FIG. 4B is the image from FIG. 4A after applying a threshold to identify areas of increased surface potential. The dark regions show areas of the image which are greater than a positive threshold. These regions represent areas of increased surface potential or work function and correspond to the metal pattern. The image of FIG. 4C is the image of FIG. 4A after thresholding to identify regions of decreased surface potential. Dark regions show areas of the image which are less than a negative threshold. These regions represent areas of decreased surface potential or work function, and correspond to regions of non-metallic contamination. For non-uniformities resulting from changes in the height of the wafer surface, the polarity of the non-uniformity indicates whether the wafer height at the non-uniformity is higher or lower than the surrounding area. For non-uniformities resulting from changes in surface potential, the polarity of the non-uniformity indicates if the surface potential is higher or lower at the non-uniformity. This information can be used to classify different types of chemical non-uniformities. For example, contamination of a silicon surface with some types of metals will result in an increase in surface potential, while contamination with many organics will result in a decrease in surface potential. In this case it is possible to discriminate between metal and organic contaminants based on the direction of surface potential change. Independent data from other sensors of conventional nature can be readily used to infer likely types of non-uniformity. In addition, the basic nature of a manufacturing process will provide clues as to the category of non-uniformity.

Figure 9A:
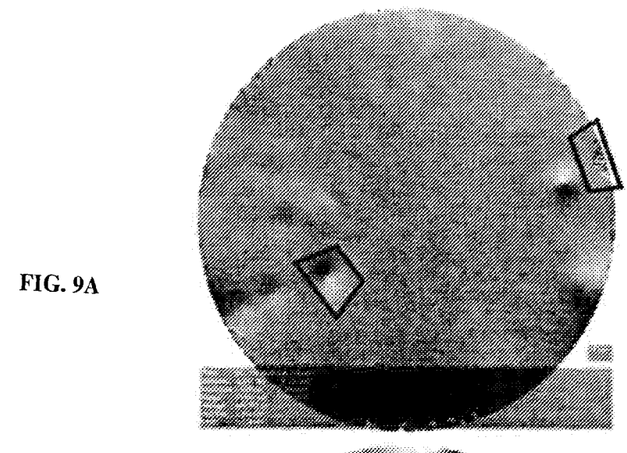
FIGS. 9A-9D show four images of the same wafer acquired by scanning the wafer with a non-vibrating contact potential difference sensor; the image of FIG. 9A is acquired with no bias voltage applied between the probe tip and the wafer surface; the image of FIG. 9B was acquired with a 5 Volt bias applied to the probe tip; and the image of FIG. 9C shows a height change feature of the wafer; and the image of FIG. 9D was formed by using the vibrating Kelvin probe mode to measure the contact potential difference between the probe tip and the wafer surface at multiple points, and then applying the negative of the average contact potential difference to the probe tip.
Figure 9B:
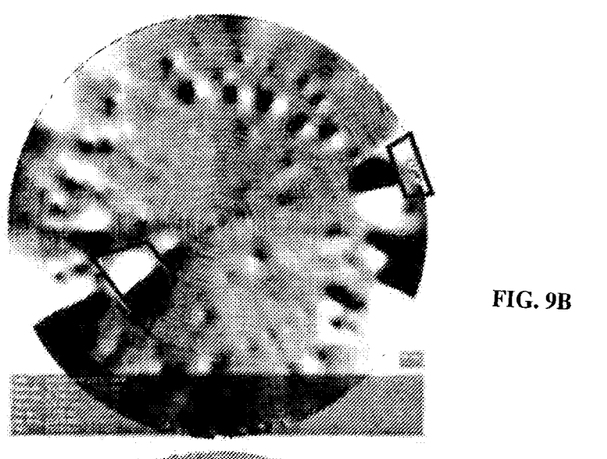
Figure 9C:
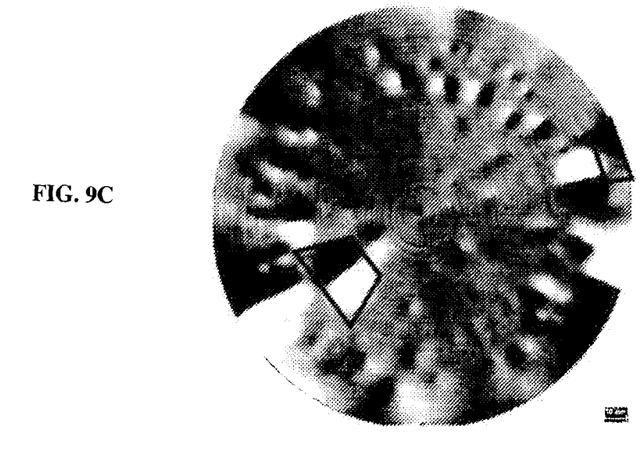
Figure 9D:
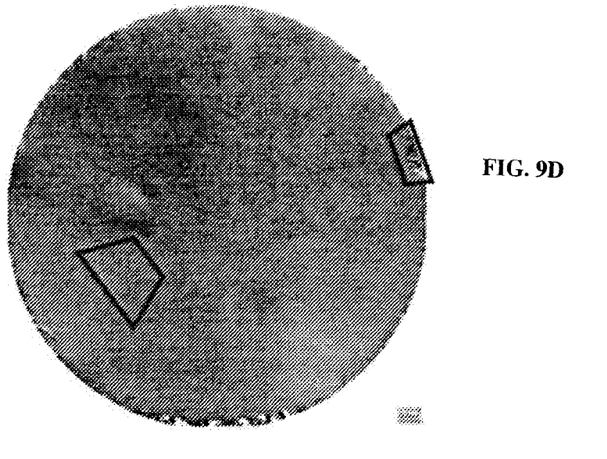

A second aspect of the invention relates to the discrimination and classification of non-uniformities as resulting from changes in capacitance between the probe tip and the wafer surface or resulting from changes in potential between the probe tip and the wafer surface (see, for example, FIGS. 9A-9D). Features in the image include both chemical non-uniformities and height changes. The highlighted feature in FIG. 9B is surface contamination which causes a change in surface potential on the wafer. The feature highlighted in FIG. 9C is a change in wafer height resulting from a particle trapped between the wafer and the vacuum chuck used to secure the wafer for scanning. The trapped particle causes a local increase in the height of the wafer surface, which results in a change in capacitance between the wafer surface and the probe tip. The signal resulting from the change in surface potential of FIG. 9B is relatively unchanged from the image of FIG. 9A, but the signal from the change in capacitance is amplified by the bias voltage. This is illustrated by the details of the image of FIG. 9B, which is formed by subtracting the image of FIG. 9A from the image of FIG. 9B. The surface potential feature is removed from the image by the subtraction operation but the change in capacitance feature remains. This technique is used to detect and classify height non-uniformities on the wafer, or to discriminate height non-uniformities from surface potential non-uniformities. The resulting scan in FIG. 9D clearly shows chemical non-uniformities, but height non-uniformities are largely eliminated. This technique is used to detect and classify non-uniformities resulting from changes is surface potential.

Figure 6A:
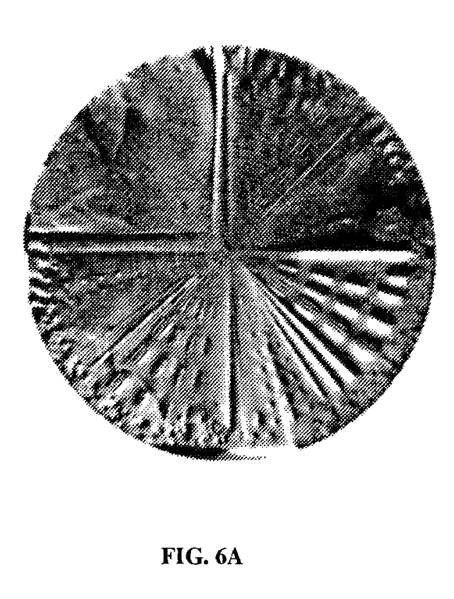
FIGS. 6A-6C show three images, and the image of FIG. 6A was acquired by scanning a wafer with a non-vibrating contact potential difference sensor with a 5 Volt bias applied to the probe tip; the image of FIG. 6B is an image of the same wafer with a −5 Volt bias applied to the probe tip, and the image of FIG. 6C is the difference of the images of FIGS. 6A and 6B.
Figure 6B:
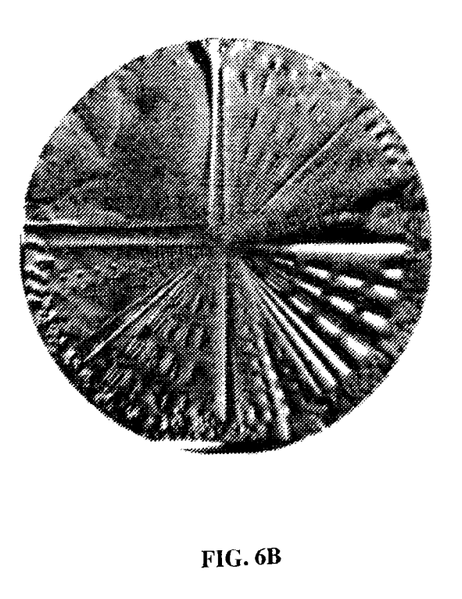
Figure 6C:
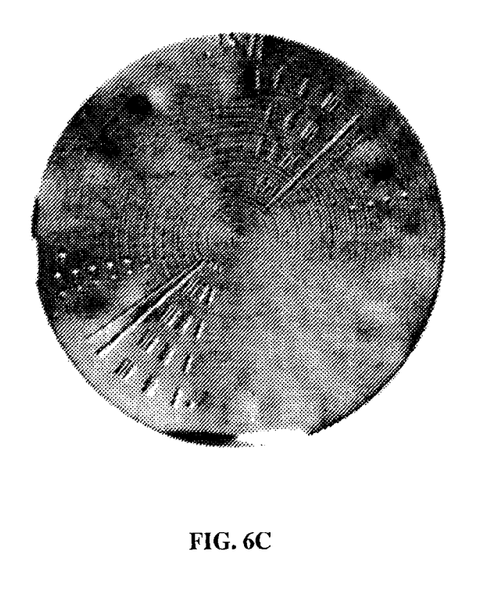

The wafer may be scanned twice with different bias voltages and one image subtracted from the other to form a new image that minimizes the signal resulting from surface potential non-uniformities and increases the signal resulting from wafer height non-uniformities. Non-uniformities which are detected in the resulting image are classified as height non-uniformities (see also FIGS. 6A-6C). FIGS. 6A-6C show three images, and the image of FIG. 6A was acquired by scanning a wafer with a non-vibrating contact potential difference sensor with a 5 Volt bias applied to the probe tip. The non-uniformities in the upper right and lower left quadrants of the wafer are etched trenches in the silicon. The signal from these features is generated by changes in the height of the wafer surface which induces a capacitance change between the sensor probe tip and the wafer. The non-uniformities in the lower right quadrant are a thin film of metal. The signal from these features is generated by a change in surface potential; the image of FIG. 6B is an image of the same wafer with a −5 Volt bias applied to the probe tip, and the image of FIG. 6C is the difference of the images of FIGS. 6A and 6B. The etched trenches are clearly visible; but the other features, which result from surface chemistry changes, are eliminated. These images demonstrate the use of subtracting two images acquired with different bias voltages to identify features that are caused by height non-uniformities. In addition, a vibrating Kelvin probe measurement of the contact potential difference between the probe tip and the wafer surface can be made at one or more points on a wafer. This measurement can determine the average contact potential difference between the probe tip and the wafer surface; or the average contact potential difference of a particular type of wafer can be determined by measuring one or more wafers of that type. A bias voltage that is equal in magnitude but opposite in sign to this average contact potential difference can be applied to subsequent scans to minimize the signal resulting from changes in capacitance between the probe tip and the wafer surface. Non-uniformities in the resulting image are classified as changes in wafer surface potential as opposed to changes in capacitance.

A third aspect of this invention is the identification or classification of non-uniformities based on shape or signal value statistics. After non-uniformities in or on the wafer have been identified from the non-vibrating contact potential difference image, or from an integrated version of the image, then these non-uniformities can be classified based on features extracted from the differential image, the integrated image or from an integrated image scaled to vibrating Kelvin probe measurements. These features can consist of values describing the shape of the non-uniformity; such as area, perimeter, height and width; or the signal values associated with the non-uniformity; such as standard deviation, maximum, minimum, range, and average. In addition, features describing the position of the non-uniformity on the wafer or the relative positions of non-uniformities can be used to classify non-uniformities.

Figure 5A:
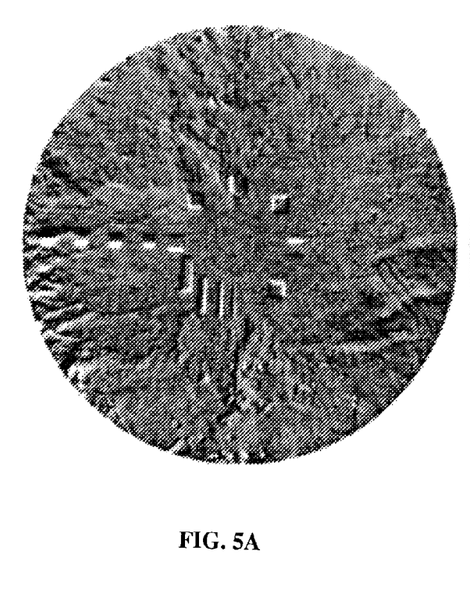
Figure 5B:
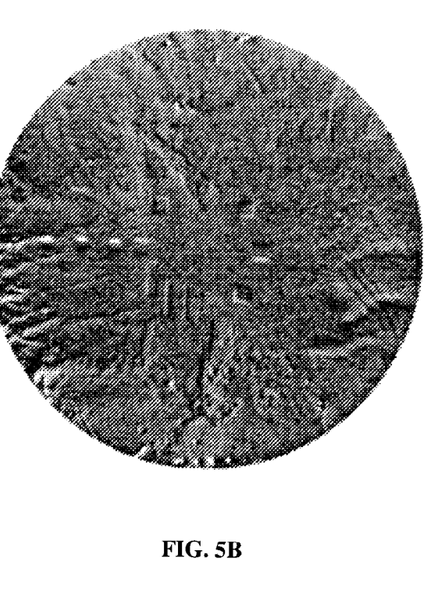
FIG. 5B was created by scanning the same wafer with the surface illuminated by visible light.
Figure 5C:
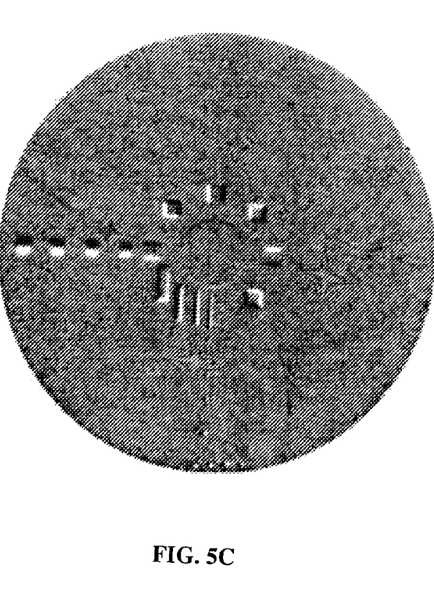
FIG. 5C is the difference between the images of FIG. 5A and FIG. 5B.

A fourth aspect of this invention is the classification of non-uniformities based on the sensitivity of the non-uniformity to light or surface deposited charge. Some types of non-uniformities, such as doping or implant non-uniformities, or charging in or on a dielectric film on or in a semiconductor substrate, are sensitive to surface illumination or charging. Two images can be acquired with different surface illumination conditions and the images subtracted. The resulting image shows changes in surface potential with illumination (see FIGS. 5A-5C). FIGS. 5A-5C show three images, and the image of FIG. 5A was created by scanning a wafer with a non-vibrating contact potential difference sensor with no surface illumination; FIG. 5B was created by scanning the same wafer with the surface illuminated by visible light; and FIG. 5C is the difference between the images of FIG. 5A and FIG. 5B. The features that are visible in the image of FIG. 5C were created by implanting dopants in the wafer. Images acquired with different levels of super bandgap illumination can be subtracted and used to detect or classify defects which are sensitive to illumination, such as doping or implant non-uniformity, or charging in or on a dielectric film on a semiconductor substrate. This image is sometimes called a Surface Photo Voltage (SPV) image. The surface photo voltage image can be processed to identify and classify non-uniformities that are sensitive to light, such as implant non-uniformities or dielectric charging. Likewise, two images can be acquired with different charge conditions and subtracted. The resulting image can be used to detect non-uniformities that are sensitive to surface charge conditions.

A fifth aspect of this invention is the classification of non-uniformities based on the results of subsequent vibrating contact potential difference measurements. The non-vibrating contact potential difference sensor produces differential data that represents changes in surface potential or height across the wafer. Vibrating Kelvin probe measurements, however, provide a measure of the absolute contact potential difference between the sensor probe tip and the wafer surface (see FIG. 8). Measurements were made on a silicon surface contaminated with both metallic and organic contaminants. The organic contaminants result in lower contact potential difference values than the metallic contaminants. Once non-uniformities have been identified and located using the non-vibrating sensor image, or an integrated version of the image, then vibrating Kelvin probe measurements can be made at the locations of the non-uniformities (see, for example, FIG. 7). Features in each quadrant of FIG. 7 were created by applying different metals to the surface of the wafer. Vibrating contact potential difference sensor measurements were then made at the locations of non-uniformities identified in each quadrant. The vibrating contact potential difference measurements show different surface potential values for each of the metals, illustrating how vibrating contact potential difference sensor measurements can be used to classify defects detected by the non-vibrating contact potential difference scanned image. The contact potential difference as measured by the vibrating Kelvin probe usually varies with surface chemistry and these measurements can provide information that is useful in classifying surface non-uniformities. In addition, some types of non-uniformities, such as charges (deposited or otherwise present) trapped in or on a dielectric deposited on the surface of the wafer, can create relatively large contact potential difference measurements. Charging non-uniformities that produce relatively large signals can be classified based on the magnitude of the measurement and also on changes of the level of signal. For example, a contact potential difference measurement of over one Volt is often due to charging in a dielectric.

Figure 7:
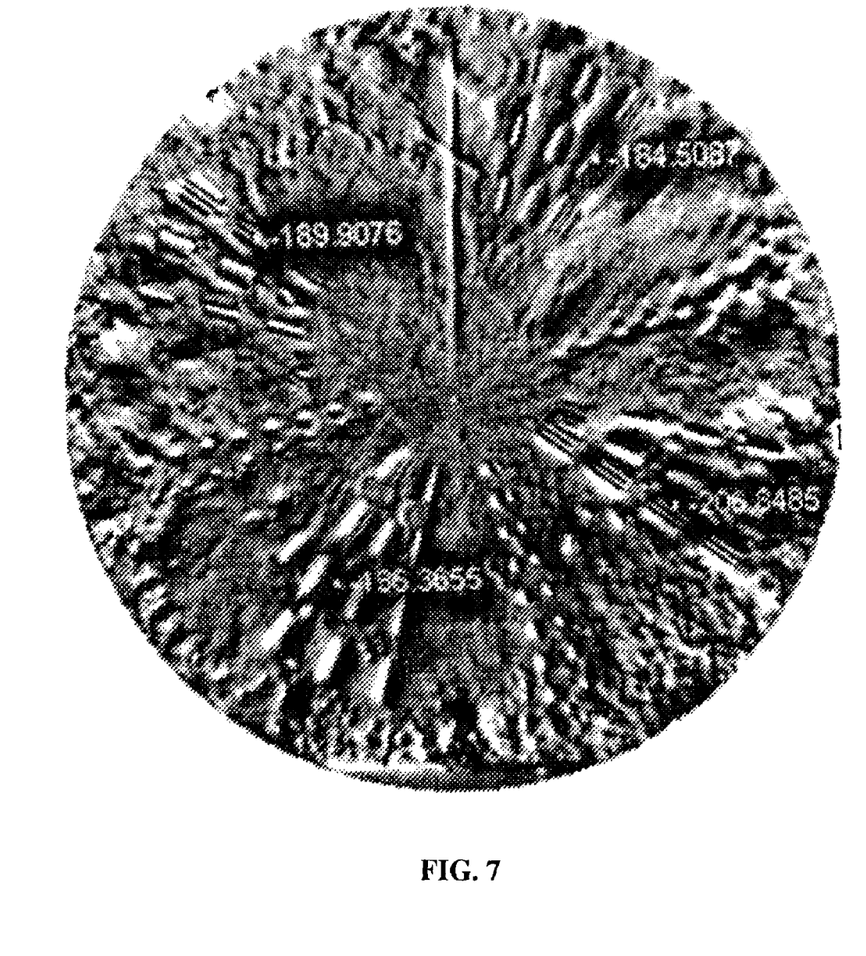
FIG. 7 shows an image of a wafer acquired by scanning with a non-vibrating contact potential difference sensor.
Figure 8:
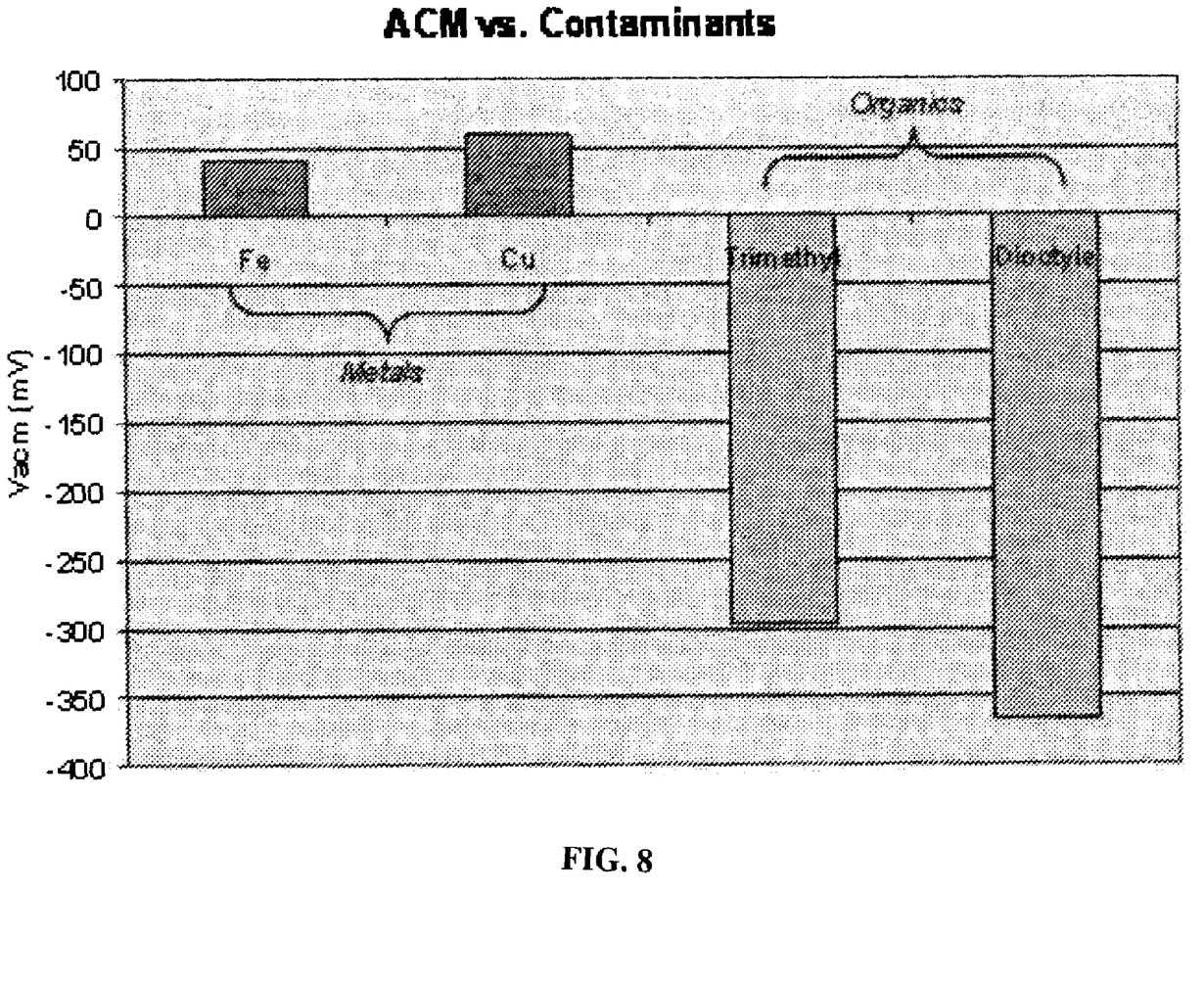
FIG. 8 shows Absolute CPD Measurements (ACMs) acquired with a vibrating Kelvin probe.

A sixth aspect of this invention is the classification of non-uniformities based on contact potential difference values obtained by scaling integrated non-vibrating contact potential difference image to two or more vibrating contact potential difference measurements (see FIG. 7). The resulting image values represent approximate contact potential difference values at each point in the image. These values can be used much like vibrating contact potential difference measurements to classify non-uniformities based on absolute contact potential difference values. The resulting image is useful for identifying regions with specific surface potential values, and is particularly useful for detecting and classifying areas of large contact potential difference that typically result from charging in or on a dielectric.

There are many alternate mechanical configurations and scanning operations that would accomplish the same result as the embodiment described above. For example, the non-vibrating contact potential difference sensor 101, height sensor 111, illumination source 109, charge source 110, and system for vibrating the sensor 104 could all be mounted at fixed locations, and the wafer 105 could be moved and rotated beneath these stationary elements. Instead of stepping from one radius to the next, the non-vibrating contact potential difference sensor 101 could be moved continuously along the wafer 105 radius while the wafer 105 is spinning to create a continuous stream of data that spirals across the whole surface of the wafer 105. Also, instead of the radial scanning operation described above, the non-vibrating contact potential difference sensor 101 could be moved linearly across the wafer 105 in a back-and-forth manner to scan the entire wafer surface 106. Also, multiple non-vibrating contact potential difference sensors and illumination sources could be used to acquire multiple measurements simultaneously to reduce the time required to measure a wafer.

The foregoing description of embodiments of the present invention have been presented for purposes of illustration and description. It is not intended to be exhaustive or to limit the present invention to the precise form disclosed, and modifications and variations are possible in light of the above teachings or may be acquired from practice of the present invention. The embodiments were chosen and described in order to explain the principles of the present invention and its practical application to enable one skilled in the art to utilize the present invention in various embodiments, and with various modifications, as are suited to the particular use contemplated

What is claimed is:

1. A method of classifying a non-uniformity of a semiconductor wafer, comprising the steps of:
    providing a semiconductor comprising a wafer having a wafer surface;
    providing a contact potential difference sensor having a probe tip;
    scanning the wafer surface laterally relative to the contact potential difference sensor;
    generating sensor data representative of changes in contact potential difference between the sensor probe tip and the wafer surface as the sensor probe tip scans laterally relative to the wafer surface;
    using the contact potential difference sensor data to detect wafer non-uniformities;
    processing the contact potential difference sensor data at the location of a non-uniformity by performing the steps of integrating the potential difference sensor data wherein integrated sensor data is indicative of relative surface potential, testing the integrated sensor data by performing a threshold test to identify regions of the integrated sensor data which lie within at least one of (1) in a specific range, (2) above a specified value and (3) below a specified value, thereby determining polarity at the non-uniformity and detecting a direction of change to one of lower or higher surface potential of the wafer surface; and
    using the direction of change to one of lower or higher of surface potential as one feature to classify the wafer non-uniformity.

2. The method as defined in claim 1 further including separating the sensor data between spatial change and chemical change on the wafer surface.

3. The method of claim 2 further including the steps of varying a bias voltage applied between the probe tip and the wafer surface, wherein the change in the sensor data resulting from varying the bias voltage applied to the probe tip or wafer surface is used to classify the non-uniformity as resulting from a change in one of wafer height and a change in chemical state of the wafer surface.

4. The method as defined in claim 1 where the non-uniformity is classified as either metal or non-metal.

5. The method as defined in claim 1 further including the step of providing independent data characteristic of the likelihood of the non-uniformity being a chemical change and being one of metal contamination and non-metal contamination and using the independent data and the direction of change of surface potential to analyze the type of non-uniformity.

6. The method as defined in claim 1 wherein the step of using the direction of change includes measurin&an increase in surface potential which is indicative of a metal contamination and measuring a decrease of surface potential which is indicative of an organic contamination.

7. The method of claim 1, further including applying a bias voltage to the sensor probe tip or the wafer surface to minimize average differences in the potential difference sensed, thereby minimizing the signal component arising from changes in distance between the probe tip and the wafer surface.

8. The method of claim 7 wherein the bias voltage that minimizes the average contact potential difference between the probe tip and the wafer surface is calculated as the average of at least one vibrating Kelvin probe measurement made on a representative test wafer surface.

9. The method of claim 1 further including the step of applying an illumination to the wafer surface.

10. The method of claim 1 further including the step of characterizing shape of the non-uniformity from the sensor data in order to correlate to a particular type of the non-uniformity.

11. The method of claim 1 further including the step of classifying a non-uniformity by vibrating a Kelvin probe at the location of the non-uniformity and sensing an associated signal.

12. The method of claim 11 further including the step of classifying a non-uniformity by measuring charge present at least one of on the wafer surface, on a dielectric film present on the wafer surface, and in the dielectric film present on the wafer surface based on the magnitude of a measurement of vibrating the Kelvin probe.

13. The method of claim 11 wherein the at least one vibrating Kelvin probe measurement is compared to vibrating Kelvin probe measurements on known contaminants to classify the non-uniformity.

14. The method of claim 11 wherein the step of classifying a non-uniformity comprises measuring the sensor data at a location of a non-uniformity in an image that is formed by integrating the non-vibrating contact potential difference sensor data and transforming resulting integrated data into absolute contact potential difference values based on at least two vibrating Kelvin probe measurements on the wafer surface.

15. A system for classifying non-uniformity type of a semiconductor wafer comprising:
    a potential difference sensor to produce a sensor signal;
    a wafer fixture to hold a semiconductor wafer and a mechanism to scan the wafer relative to the potential difference sensor and to rotate a spindle coupled to the wafer fixture, thereby enabling relative motion between the wafer and the sensor; and
    a source of independent data indicative of whether a non-uniformity type is a metallic contaminant or nonmetallic contaminant based on a direction of change of the sensor signal to a positive or negative change of surface potential, thereby enabling determination of the non-uniformity type on the wafer.

16. The system as defined in claim 15 further including a bias voltage source for applying a bias voltage to at least one of the wafer and the sensor, thereby enabling minimizing average differences in potential differences sensed to minimize a signal component arising from changes in distance between the sensor and a surface of the wafer.

17. The system as defined in claim 15 further including a vibrating Kelvin probe which measures a vibrating probe potential difference at selected locations of a non-uniformity.

18. The system as defined in claim 17 further including a device to deposit charge on a surface of the wafer, thereby enabling the classification of a non-uniformity by measuring a change in signal induced by the charge deposited on the surface of the wafer by use of the vibrating Kelvin probe.

19. The system as defined in claim 15 further including a source of light which can be applied to the wafer at selected angles of inclination with variable light intensity and variable wavelength, thereby enabling further probing of the wafer.

20. The system as defined in claim 19 wherein the source of light can be controlled to vary at least one of the light intensity and the wavelength for classifying the non-uniformity of the wafer of the semiconductor wafer.

21. A system for classifying non-uniformity type of a semiconductor wafer comprising:

a potential difference sensor to produce a sensor signal;

a wafer fixture to hold a semiconductor wafer and a mechanism to scan the wafer relative to the potential difference sensor and to rotate a spindle coupled to the wafer fixture, thereby enabling relative motion between the wafer and the sensor; and a source of data indicative of whether a non-uniformity type is one of a metallic contaminant, nonmetallic contaminant and excess electronic charge based on the type of sensor signal, thereby enabling determination of the non-uniformity type on the wafer.

* * * * *